US008470305B2

(12) United States Patent
Johnson et al.

(10) Patent No.: US 8,470,305 B2
(45) Date of Patent: *Jun. 25, 2013

(54) SHAMPOO CONTAINING A GEL NETWORK

(75) Inventors: Eric Scott Johnson, Hamilton, OH (US); Benjamin Parker Heath, Cincinnati, OH (US); Brian Michael Hurley, Blanchester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 702 days.

This patent is subject to a terminal disclaimer.

(21) Appl. No.: 11/952,380

(22) Filed: Dec. 7, 2007

(65) Prior Publication Data
US 2008/0187507 A1 Aug. 7, 2008

Related U.S. Application Data

(63) Continuation-in-part of application No. 11/228,770, filed on Sep. 16, 2005, now Pat. No. 8,349,301, which is a continuation-in-part of application No. 10/454,433, filed on Jun. 4, 2003, now Pat. No. 7,303,744.

(60) Provisional application No. 60/385,641, filed on Jun. 4, 2002.

(51) Int. Cl.
*A61Q 5/02* (2006.01)

(52) U.S. Cl.
USPC .................. 424/70.1; 424/70.27; 424/70.28

(58) Field of Classification Search
None
See application file for complete search history.

(56) References Cited

U.S. PATENT DOCUMENTS

| | | |
|---|---|---|
| 2,396,278 A | 3/1946 | Lind et al. |
| 2,438,091 A | 3/1948 | Lynch et al. |
| 2,486,921 A | 11/1949 | Byerly et al. |
| 2,486,922 A | 11/1949 | Strain et al. |
| 2,528,378 A | 10/1950 | Manheimer et al. |
| 2,658,072 A | 11/1953 | Kosmin et al. |
| 2,694,668 A | 11/1954 | Pricke et al. |
| 2,786,847 A | 3/1957 | Cislak et al. |
| 2,798,053 A | 7/1957 | Brown et al. |
| 2,809,971 A | 10/1957 | Berstein et al. |
| 2,826,551 A | 3/1958 | Geen et al. |
| 3,152,046 A | 10/1964 | Kapral et al. |
| 3,155,591 A | 11/1964 | Hilfer et al. |
| 2,326,733 A | 2/1966 | Karsten et al. |
| 3,236,733 A | 2/1966 | Karsten et al. |
| 3,332,880 A | 7/1967 | Kessler et al. |
| 3,589,999 A | 6/1971 | McRae et al. |
| 3,590,035 A | 6/1971 | Damico et al. |
| 3,753,196 A | 8/1973 | Kurtz et al. |
| 3,761,418 A | 9/1973 | Parran et al. |
| 3,773,770 A | 11/1973 | Damico et al. |
| 3,852,441 A | 12/1974 | Kooistra et al. |
| 3,929,678 A | 12/1975 | Laughlin et al. |
| 3,940,482 A | 2/1976 | Grand |
| 3,958,581 A | 5/1976 | Abegg et al. |
| 3,959,461 A | 5/1976 | Bailey et al. |
| 3,964,500 A | 6/1976 | Drakoff |
| 4,055,655 A | 10/1977 | Maurer et al. |
| 4,089,945 A | 5/1978 | Brinkman et al. |
| 4,152,416 A | 5/1979 | Spitzer et al. |
| 4,161,526 A | 7/1979 | Gorman et al. |
| 4,197,865 A | 4/1980 | Jacquet et al. |
| 4,217,914 A | 8/1980 | Jacquet et al. |
| 4,323,683 A | 4/1982 | Bolich et al. |
| 4,345,080 A | 8/1982 | Bolich et al. |
| 4,364,387 A | 12/1982 | Larkin et al. |
| 4,379,753 A | 4/1983 | Bolich et al. |
| 4,381,919 A | 5/1983 | Jacquet et al. |
| 4,387,090 A | 6/1983 | Bolich et al. |
| 4,422,853 A | 12/1983 | Jacquet et al. |
| 4,470,982 A | 9/1984 | Winkler et al. |
| 4,507,280 A | 3/1985 | Pohl et al. |
| 4,529,586 A | 7/1985 | DeMarco et al. |
| 4,565,647 A | 1/1986 | Llenado |

(Continued)

FOREIGN PATENT DOCUMENTS

| | | |
|---|---|---|
| CN | 1658830 A | 8/2005 |
| DE | 10005162 A1 | 8/2001 |

(Continued)

OTHER PUBLICATIONS

Eccleston, et al., "Functions of mixed Emulsifiers and Emulsifying Waxes in Dermatological Lotions and Cream", *Colloids and Surfaces*, May 15, 1997, pp. 169-182, vol. 123-124, A. Physicachemicl and Engineering Aspects, Elsevier, Amsterdam, NL, XP00509628.

Ribeiro, H.M., et al., "Structure and rheology of semisolid o/w creams containing cetyl alcohol/non-ionic surfactant mixed emulsifier and different polymers", *International Journal of Cosmetic Science*, 2004, pp. 47-59, vol. 26, No. 2, Blackwell Publishing Ltd, XP002413735.

Savic, Snezana et al, "Colloidal Microstructure of binary systems and model creams stabilized with an alkylpolyglucoside non-ionic emulsifier", *Colloid Polymer Science*, Springer-Verlag, Sep. 28, 2004, pp. 439-451, fig 5, vol. 283, XP002413673.

Barry & Rowe, *The Characterization by Small Angle X-Ray Scattering of a Gel with a Lamellar Structure*, International Journal of Pharmaceuticals, 1989.

(Continued)

Primary Examiner — Jyothsna Venkat
(74) Attorney, Agent, or Firm — Angela K. Haughey

(57) ABSTRACT

A shampoo composition comprising: a) from about 5% to about 50% of one or more detersive surfactants, by weight of said shampoo composition; b) a dispersed solid crystalline gel network phase comprising: i) a first component comprising at least about 0.05% of one or more fatty acids by weight of said shampoo composition; ii) a second component comprising at least about 0.05% of one or more additional fatty amphiphiles by weight of said shampoo composition; iii) water; and c) at least about 20% of an aqueous carrier, by weight of said shampoo composition; wherein said first component is combined with said second component in the ratio of 10:1 to about 1:5 to form said solid crystalline gel network phase.

5 Claims, 3 Drawing Sheets

U.S. PATENT DOCUMENTS

| | | | |
|---|---|---|---|
| 4,608,183 A | 8/1986 | Rossmoore et al. |
| 4,663,158 A | 5/1987 | Wolfram et al. |
| 4,666,616 A | 5/1987 | Rossmoore |
| 4,670,430 A | 6/1987 | Imamura et al. |
| 4,686,254 A | 8/1987 | Lochhead et al. |
| 4,704,272 A | 11/1987 | Oh et al. |
| 4,708,863 A | 11/1987 | Bews et al. |
| 4,788,006 A | 11/1988 | Bolich et al. |
| 4,834,767 A | 5/1989 | Helioff et al. |
| 4,885,107 A | 12/1989 | Wetzel et al. |
| 4,898,585 A | 2/1990 | Borsanyi et al. |
| 5,034,218 A | 7/1991 | Duvel et al. |
| 5,057,153 A | 10/1991 | Ruggiero et al. |
| 5,104,646 A | 4/1992 | Bolich et al. |
| 5,106,609 A | 4/1992 | Bolich et al. |
| 5,106,613 A | 4/1992 | Hartnett et al. |
| 5,114,898 A | 5/1992 | Pinnavaia et al. |
| 5,154,847 A | 10/1992 | LaPetina et al. |
| 5,186,928 A | 2/1993 | Birtwistle et al. |
| 5,202,048 A | 4/1993 | Bartolo et al. |
| 5,227,156 A | 7/1993 | Wiese et al. |
| 5,248,445 A | 9/1993 | Rizvi et al. |
| RE34,584 E | 4/1994 | Grote et al. |
| 5,358,667 A | 10/1994 | Bergmann et al. |
| 5,462,589 A | 10/1995 | Nicholas et al. |
| 5,466,425 A | 11/1995 | Adams et al. |
| 5,478,501 A | 12/1995 | Rau et al. |
| 5,518,774 A | 5/1996 | Kappock et al. |
| 5,540,954 A | 7/1996 | Nicholas et al. |
| 5,562,995 A | 10/1996 | Kappock et al. |
| 5,614,538 A | 3/1997 | Nelson et al. |
| 5,674,478 A | 10/1997 | Dodd et al. |
| 5,696,169 A | 12/1997 | Otsu et al. |
| 5,710,114 A | 1/1998 | Pyles et al. |
| 5,726,137 A | 3/1998 | Patel et al. |
| 5,750,122 A | 5/1998 | Evans et al. |
| 5,756,076 A | 5/1998 | Cervantes et al. |
| 5,785,962 A | 7/1998 | Hinz et al. |
| 5,798,121 A | 8/1998 | Cauwet et al. |
| 5,837,661 A | 11/1998 | Evans et al. |
| 5,853,707 A | 12/1998 | Wells et al. |
| 5,854,319 A | 12/1998 | O'Lenick et al. |
| 5,874,476 A | 2/1999 | Hsu et al. |
| 5,876,705 A | 3/1999 | Uchiyama et al. |
| 5,880,076 A | 3/1999 | Vermeer et al. |
| 5,883,154 A | 3/1999 | Kappock et al. |
| 5,939,059 A | 8/1999 | Franklin et al. |
| 5,939,203 A | 8/1999 | Kappock et al. |
| 5,955,066 A | 9/1999 | Sako et al. |
| 5,965,515 A | 10/1999 | Rau et al. |
| 5,997,851 A | 12/1999 | Cox et al. |
| 6,017,562 A | 1/2000 | Kaufman et al. |
| 6,034,043 A | 3/2000 | Fujiwara et al. |
| 6,303,109 B1 | 10/2001 | Foerster et al. |
| 6,309,628 B1 | 10/2001 | Ansmann et al. |
| 6,333,040 B1 | 12/2001 | Boyxen et al. |
| RE37,793 E | 7/2002 | Domenico et al. |
| 6,495,538 B2 | 12/2002 | Fliss et al. |
| 6,521,238 B1 | 2/2003 | Muller et al. |
| RE38,130 E | 6/2003 | Adams |
| 6,719,967 B1 | 4/2004 | Brown |
| 6,774,096 B1 | 8/2004 | Paye et al. |
| 6,908,912 B2 | 6/2005 | Rioux et al. |
| 7,303,744 B2 * | 12/2007 | Wells et al. ............... 424/70.28 |
| 2001/0047039 A1 | 11/2001 | McManus et al. |
| 2002/0012646 A1 | 1/2002 | Royce et al. |
| 2002/0119113 A1 | 8/2002 | Ellis et al. |
| 2002/0169283 A1 | 11/2002 | Lu et al. |
| 2003/0095938 A1 | 5/2003 | Casero |
| 2003/0119805 A1 | 6/2003 | Fliss |
| 2003/0130145 A1 | 7/2003 | Patel et al. |
| 2003/0171231 A1 | 9/2003 | Shana'a et al. |
| 2003/0185779 A1 | 10/2003 | Mitsumatsu et al. |
| 2003/0215522 A1 | 11/2003 | Johnson et al. |
| 2003/0223952 A1 | 12/2003 | Wells et al. |
| 2003/0224955 A1 | 12/2003 | Ribery et al. |
| 2004/0058855 A1 | 3/2004 | Schwartz et al. |
| 2004/0167114 A1 | 8/2004 | Fliss |
| 2004/0191331 A1 | 9/2004 | Schwartz et al. |
| 2004/0197294 A1 | 10/2004 | Seipel et al. |
| 2004/0223941 A1 | 11/2004 | Schwartz et al. |
| 2004/0234471 A1 | 11/2004 | Corbella |
| 2004/0266886 A1 | 12/2004 | Seipel et al. |
| 2005/0031569 A1 | 2/2005 | Seipel et al. |
| 2005/0143268 A1 | 6/2005 | Midha et al. |
| 2005/0181067 A1 | 8/2005 | Yokoyama et al. |
| 2005/0202984 A1 | 9/2005 | Schwartz et al. |
| 2006/0024256 A1 | 2/2006 | Wells et al. |
| 2006/0024381 A1 | 2/2006 | Schwartz et al. |
| 2006/0045861 A1 | 3/2006 | Bejger et al. |
| 2006/0251605 A1 | 11/2006 | Belmar |
| 2006/0269501 A1 | 11/2006 | Johnson et al. |
| 2006/0269502 A1 | 11/2006 | Johnson et al. |
| 2007/0110696 A1 | 5/2007 | Johnson et al. |
| 2007/0110700 A1 | 5/2007 | Wells et al. |
| 2007/0128147 A1 | 6/2007 | Schwartz et al. |
| 2008/0152611 A1 | 6/2008 | Wells et al. |
| 2008/0187507 A1 | 8/2008 | Johnson et al. |

FOREIGN PATENT DOCUMENTS

| | | |
|---|---|---|
| EP | 0037318 A1 | 10/1981 |
| EP | 0077630 | 4/1985 |
| EP | 0555690 | 8/1993 |
| EP | 0627216 A2 | 12/1994 |
| EP | 0976393 A1 | 2/2000 |
| EP | 1123693 | 2/2000 |
| EP | 1082086 | 3/2001 |
| EP | 1161869 | 12/2001 |
| FR | 2478467 | 9/1981 |
| FR | 2593801 | 8/1987 |
| GB | 849433 | 9/1960 |
| GB | 2177108 | 1/1987 |
| GB | 2177108 A | 1/1987 |
| JP | 52/092881 | 8/1977 |
| JP | 6134227 | 5/1994 |
| JP | 7118103 | 5/1995 |
| JP | 2000/103724 | 4/2000 |
| JP | 2001181145 A2 | 7/2001 |
| JP | 2001311099 A2 | 11/2001 |
| JP | 2002/104940 | 4/2002 |
| JP | 2002-104940 | 10/2002 |
| JP | 2004/262805 | 9/2004 |
| JP | 2004-262805 A1 | 9/2004 |
| JP | 2004/292387 | 10/2004 |
| JP | 2004-292387 A | 10/2004 |
| JP | 2004/292390 | 10/2004 |
| JP | 2004-292390 | 10/2004 |
| JP | 2004/307463 | 11/2004 |
| JP | 2004-307463 A | 11/2004 |
| JP | 2005/022983 | 1/2005 |
| JP | 2005-022983 A | 1/2005 |
| JP | 2005/187342 A | 7/2005 |
| JP | 2006063044 A2 | 3/2006 |
| WO | WO-93/08787 A2 | 5/1993 |
| WO | WO 9308787 | 5/1993 |
| WO | WO 9410973 | 5/1994 |
| WO | WO-95/01152 A1 | 1/1995 |
| WO | WO 9501152 | 1/1995 |
| WO | WO 9625913 | 8/1996 |
| WO | WO-97/14396 A1 | 4/1997 |
| WO | WO 9714396 | 4/1997 |
| WO | WO 9847372 | 10/1998 |
| WO | WO 99/38475 * | 8/1999 |
| WO | WO 9938475 | 8/1999 |
| WO | WO-99/51199 A1 | 10/1999 |
| WO | WO 9951199 | 10/1999 |
| WO | WO 9959540 | 11/1999 |
| WO | WO 0066081 | 11/2000 |
| WO | WO-01/00149 A1 | 1/2001 |
| WO | WO 0100149 | 1/2001 |
| WO | WO 01/17492 * | 3/2001 |
| WO | WO 0117492 | 3/2001 |
| WO | WO-01/39735 A1 | 6/2001 |
| WO | WO 0139735 | 6/2001 |
| WO | WO-01/78657 A | 10/2001 |
| WO | WO 0178657 | 10/2001 |
| WO | WO-02/22091 A2 | 3/2002 |

| | | |
|---|---|---|
| WO | WO 0219977 | 3/2002 |
| WO | WO 0222091 | 3/2002 |
| WO | WO 0232361 | 4/2002 |
| WO | WO 02076422 | 10/2002 |
| WO | WO 02080943 | 10/2002 |
| WO | WO 03032934 | 4/2003 |
| WO | WO-03/101418 A | 12/2003 |
| WO | WO 03101418 | 12/2003 |
| WO | WO 2005/048959 | 6/2005 |
| WO | WO-2005/48959 A | 6/2005 |

OTHER PUBLICATIONS

Barry & Saunders, *Kinetics of Structure Build-up in Self Bodied Emulsions Stabalized by Mixed Emulsifiers*, Journal of Colloid Science, vol. 41, 1972.

Barry, B.W., Structure and Rheology of Emulsions Stabalized by Mixed Emulsifiers, British Society of Rheology, 1970.

Benton et al, Phase Behavior and Network Formation in a Cationic Surfactant-Fatty Alcohol System, JAOCS, vol. 64, 1987.

Burgess, J.D., Practical Analysis of Complex Coacervate Systems, Journal of Colloid Science, vol. 140, 1990.

CTFA Cosmetic Ingredient Dictionary, 1982, 3rd Edition, The Cosmetic, Toiletry & Fragrance Association, Inc., Washington, DC (book not included).

1—Eccleston, G.M., *Application of Emulsion Stability Theories to Mobile and Semisolid o/w Emulsions*, Cosmetics Magazine, vol. 101, 1986.

2—Eccleston, G.M., *Application of Emulsion Theory to Complex and Real Systems*, International Journal of Cosmetic Science, 1985.

3—Eccleston, G.M., *Formulating Cosmetic Emulsions*, Cosmetics Magazine, vol. 112, 1997.

4—Eccleston, G.M., *Functions of Mixed Emulsifiers and Emulsifying Waxes in Dermatological Lotions and Creams*, Colloids and Surfaces, vol. 123, 1997.

5—Eccleston, G.M., *Microstructural Changes During Storage of Cetostearyl Alcohol/Polyoxyethylene Alkyl Ether Surfactants*, University of Strathclyde, 1988.

6—Eccleston, G.M., *Multiple Phase Oil and Water Emulsions*, Journal of Cosmetic Chemists, 1990.

7—Eccleston, G.M., *Structure and Rheology of Semisolid o/w Creams Containing Cetyl Alcohol/Non-ionic Surfactant Mixed Emulsifier and Different Polymers*, International Journal of Cosmetic Science, 2004.

8—Eccleston, G.M., Synchrotron X-ray Investigations into the Lamellar Gel Phase Formed in Creams Prepared with Fatty Alcohols, International Journal of Pharmaceuticals, 2000.

9—Eccleston, G.M., The Influence of Fatty Alcohols on the Structure and Stability of Creams Preapred with Fatty Alcohols, International Journal of Cosmetic Science, 1982.

Encyclopedia of Polymer Science and Engineering, John Wiley & Sons, vol. 15, 1989 (book not included).

Griffin, W.C., Calculation of HLB Values of Non-Ionic Surfactants, Journal of the Society of Cosmetic Chemists; 1954. vol. 5, pp. 249-235.

Korhonen et al, Rheological Properties of Three Component Creams Containing Sorbitan Monoesters as Surfactants, International Journal of Pharmaceuticals, 2002.

Louden et al, A Preliminary Examination of the Structure of Gels and Emulsions Containing Cetostearyl Alcohol, International Journal of Pharmaceuticals, 1985.

McCutcheon, Emulsifiers and Detergents, MC Pub Company, 1989 (book not included).

Noll, W., Chemistry and Technology of Silicones, Academic Press, 1968 (book not included).

Patel et al, Properties of Cetrimide / Cetostearyl Alcohol Ternary Gels; Preparation Effects, International Journal of Pharmaceuticals, 1985.

Savic et al, *Colloidal Microstructure of Binary Systems and Model Creams Stablized with an Alkylpolyglucoside Emulsifier*, Colloid Polymer Science, vol. 283, 2004.

Saxton, C., *Antiplaque Effects and Mode of Action of a Combination of Zinc Citrate and a Nonionic Antimicrobial Agent*, Scandinavian Journal, vol. 96, 1988.

Suzuki et al, *Secondary Droplet Emulsion: Mechanism & Effects of Liquid Crystal Formation in o/w Emulsion*, Journal of Dispersion Science, 1984.

Van Cutsem, Journal of the American Academy of Dermatology, XP-002288119, 1998.

Van Oss, C.J., Coacervation, Complex Coacervation and Flocculation, Journal of Dispersion Science, vol. 9, 1989.

Yoon et al, *A Study of Gel Structure in the Nonionic Surfactant / Cetostearyl Alcohol / Water Ternary Systems by Differential Scanning Calorimeter*, Journal of Dispersion Science, 1999.

\* cited by examiner

Gel Network Example #9

Gel Network Example #12

Shampoo Example #1 with
Gel Network Example #8

Shampoo Example #2 with
Gel Network Example #9

Shampoo Example #4 with
Gel Network Example #12

SHAMPOO CONTAINING A GEL NETWORK

CROSS REFERENCE TO RELATED APPLICATION

This application is a continuation-in-part of prior U.S. application Ser. No. 11/228,770, filed on Sep. 16, 2005, now granted as U.S. Pat. No. 8,349,301, which is a continuation-in-part of U.S. application Ser. No. 10/454,433 now granted as U.S. Pat. No. 7,303,744, filed on Jun. 4, 2003, which, in turn, claims the benefit of U.S. Provisional Application Ser. No. 60/385,641, filed on Jun. 4, 2002.

FIELD OF THE INVENTION

The present invention relates to a hair cleansing and conditioning shampoo containing a gel network comprising a fatty acid.

BACKGROUND OF THE INVENTION

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying, which can interfere with combing and result in a condition commonly referred to as "fly-away hair."

A variety of approaches have been developed to alleviate these after-shampoo problems. These approaches range from post-shampoo application of hair conditioners such as leave-on and rinse-off products, to hair conditioning shampoos which attempt to both cleanse and condition the hair from a single product.

In order to provide hair conditioning benefits in a cleansing shampoo base, a wide variety of conditioning actives have been proposed. However, many of these actives have the disadvantage of leaving the hair feeling soiled or coated and of interfering with the cleansing efficacy of the shampoo.

Coacervate formation in a shampoo composition is known to be advantageous for providing conditioning benefits to the hair. However, these shampoo compositions are good for delivering wet hair conditioning but are not capable of delivering satisfactory dry hair smooth feel.

Based on the foregoing, there is a need for a conditioning shampoo which can provide improved conditioning benefit for dry hair, while not interfering with the cleansing efficacy, nor providing negative feel to the hair when it is dried. Specifically, there is a need to provide long lasting moisturized feel, smooth feel, and manageability control to the hair when the hair is dried, yet not leave the hair feeling greasy, as well as to provide softness and ease of combing when the hair is wet.

SUMMARY OF THE INVENTION

The present invention is directed to a shampoo composition comprising: a) from about 5% to about 50% of one or more detersive surfactants, by weight of said shampoo composition; b) a dispersed solid crystalline gel network phase comprising: i) a first component comprising at least about 0.05% of one or more fatty acids by weight of said shampoo composition; ii) a second component comprising at least about 0.05% of one or more additional fatty amphiphiles by weight of said shampoo composition; iii) water; and c) at least about 20% of an aqueous carrier, by weight of said shampoo composition; wherein said first component is combined with said second component in the ratio of 10:1 to about 1:5 to form said solid crystalline gel network phase.

The present invention is also directed to a shampoo composition comprising: a) from about 5% to about 50% of one or more detersive surfactants, by weight of said shampoo composition; b) a dispersed solid crystalline gel network phase comprising: i) a first component comprising at least about 0.05% of one or more fatty acids by weight of said shampoo composition; ii) a second component comprising at least about 0.01% of one or more secondary surfactants, by weight of said shampoo composition; iii) water; and c) at least about 20% of an aqueous carrier, by weight of said shampoo composition; wherein said first component is combined with said second component in the ratio of from about 1:1 to about 40:1, to form said solid crystalline gel network phase.

The present invention also is directed to a process of making the shampoo composition described above.

These and other features, aspects, and advantages of the present invention will become evident to those skilled in the art from a reading of the present disclosure.

DETAILED DESCRIPTION OF THE INVENTION

Figure 1:
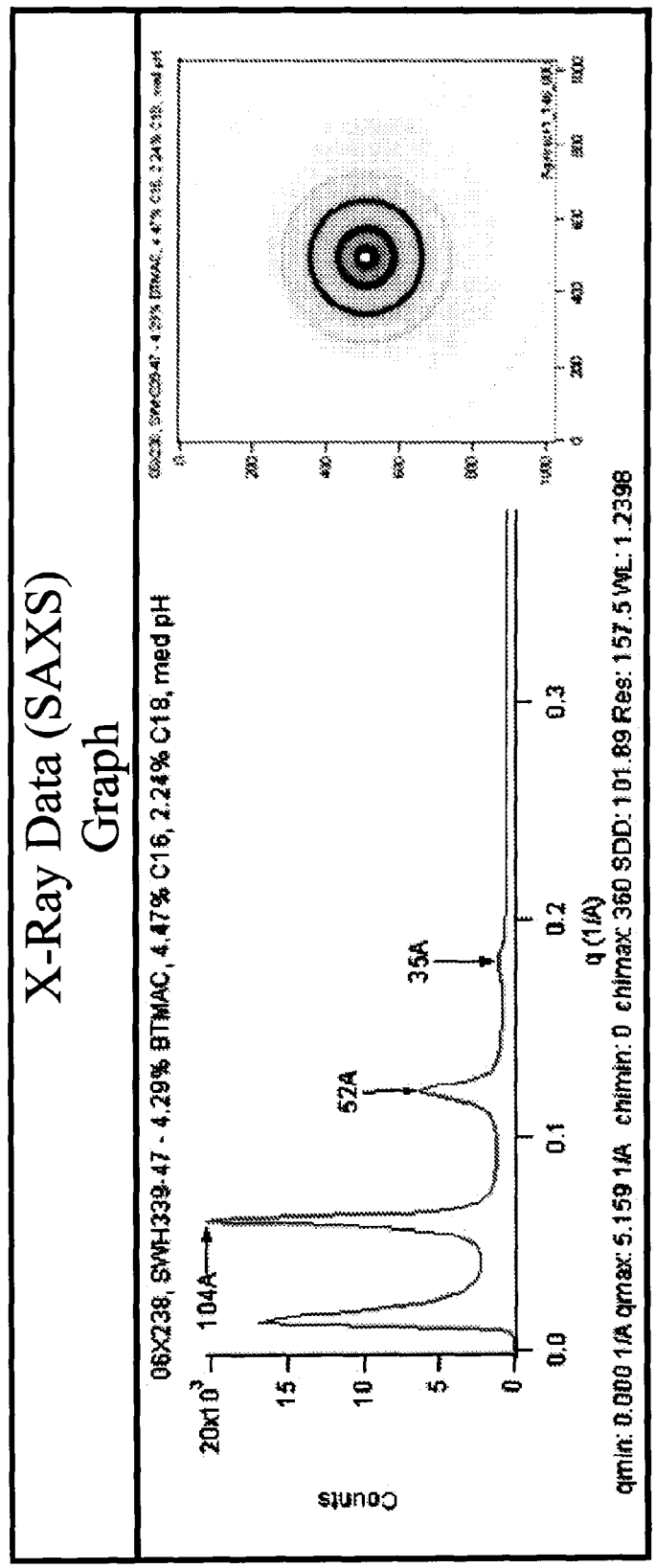
FIG. 1 is a graph of X ray data for gel network example #8.
Figure 2:
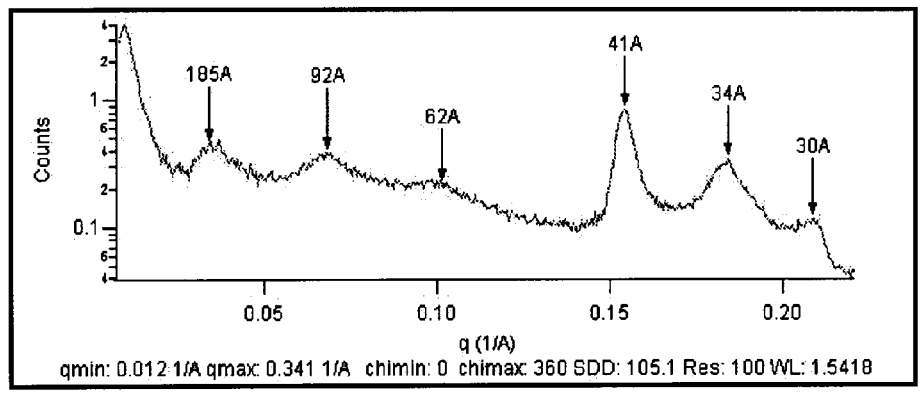
FIG. 2 is a graph of X ray data for gel network example #9.
Figure 3:
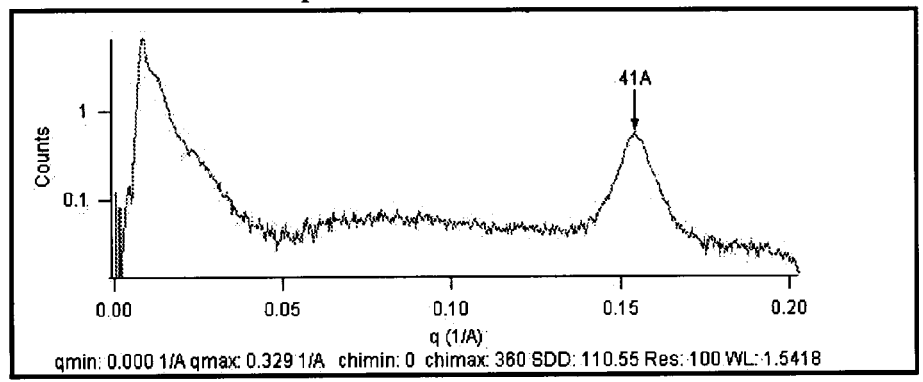
FIG. 3 is a graph of X ray data for gel network example #12.
Figure 4:
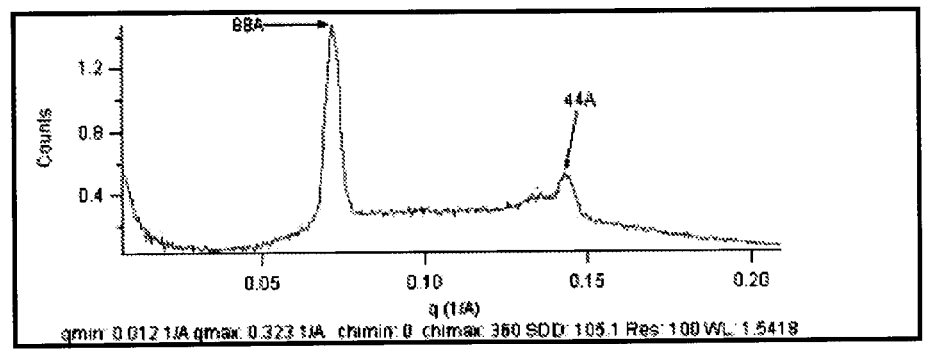
FIG. 4 is a graph of X ray data for shampoo example #1 with gel network example #8.
Figure 5:
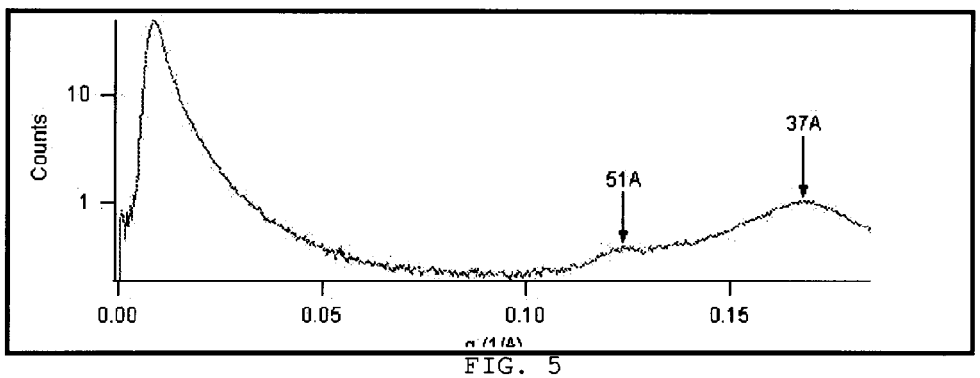
FIG. 5 is a graph of X ray data for shampoo example #2 with gel network example #9.
Figure 6:
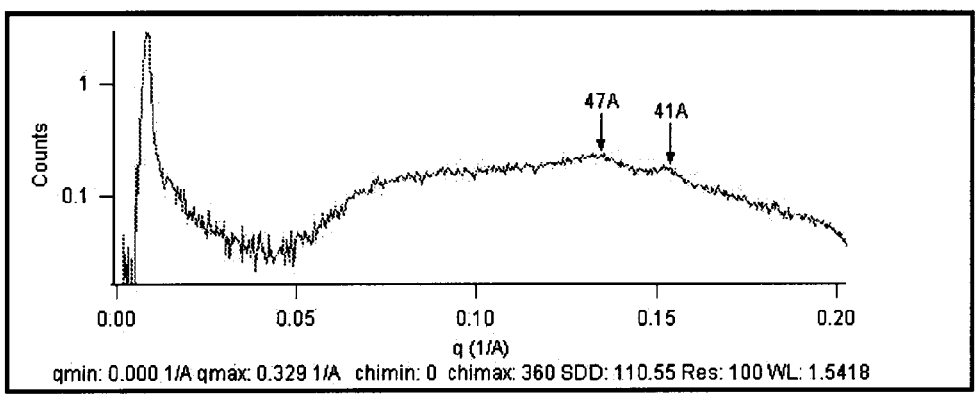
FIG. 6 is a graph of X ray data for shampoo example #4 with gel network example #12.

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

The term "charge density", as used herein, refers to the ratio of the number of positive charges on a polymer to the molecular weight of said polymer.

The term "polymer", as used herein shall include materials whether made by polymerization of one type of monomer or made by two (i.e., copolymers) or more types of monomers.

The term "shampoo", as used herein means a composition for cleansing and conditioning hair or skin, including scalp, face, and body.

The term "suitable for application to human hair", as used herein means that the compositions or components thereof so described are suitable for use in contact with human hair and the scalp and skin without undue toxicity, incompatibility, instability, allergic response, and the like.

The term "water soluble", as used herein means that the material is soluble in water in the present composition. In general, the material should be soluble at 25° C. at a concentration of 0.1% by weight of the water solvent, preferably at 1%, more preferably at 5%, more preferably at 15%.

The shampoo compositions of the present invention comprise one or more detersive surfactants, a dispersed gel network phase, and an aqueous carrier. Each of these components, as well as preferred or optional components, is described in detail hereinafter.

Detersive Surfactant

The shampoo compositions comprise one or more detersive surfactants. The detersive surfactant component is included in shampoo compositions of the present invention to provide cleansing performance. The detersive surfactant may be selected from anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components include those which are known for use in hair care or other personal care cleansing compositions. The concentration of the anionic surfactant component in the composition should be sufficient to provide the desired cleaning and lather performance, and generally range from about 5% to about 50%, preferably from about 8% to about 30%, more preferably from about 10% to about 25%, even more preferably from about 12% to about 22%, by weight of the composition.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, sodium cocoyl isethionate, and combinations thereof.

Suitable zwitterionic or amphoteric detersive surfactants for use in the composition herein include those which are known for use in hair care or other personal cleansing compositions. Concentration of such amphoteric detersive surfactants preferably ranges from about 0.5% to about 20%, preferably from about 1% to about 10%. Non-limiting examples of suitable zwitterionic or amphoteric surfactants are described in U.S. Pat. Nos. 5,104,646 and 5,106,609, both to Bolich Jr. et al.

Amphoteric detersive surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Preferred amphoteric detersive surfactants include cocoamphoacetate, cocoamphodiacetate, lauroamphoacetate, lauroamphodiacetate, and mixtures thereof.

Suitable zwitterionic detersive surfactants are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The compositions herein may further comprise additional surfactants for use in combination with the anionic detersive surfactant component described hereinbefore. Suitable additional surfactants include cationic and nonionic surfactants.

Suitable cationic surfactants include quaternary ammonium salts or amido-amines having at least one fatty chain containing at least about 8 carbon atoms and mixture thereof.

Non-limiting examples of such suitable cationic surfactants include cetrimonium chloride, stearimonium chloride, behentrimonium chloride, behenamidopropyltrimonium methosulfate, stearamidopropyltrimonium chloride, arachidtrimonium chloride, and mixtures thereof.

Suitable nonionic surfactants include nonionic surfactants having an HLB of 7 or more and comprising one or more polyethyleneoxide chains wherein each polyethyleneoxide chain contains on average at least about 5 ethylene oxide units.

Nonionic surfactants comprising one or more polyethyleneoxide chain wherein each polyethyleneoxide chain contains on average at least about 5 ethylene oxide units include polyoxyethylene alkyl ethers, polyethyleneglycol fatty acid esters, polyoxyethylene castor oil, polyoxyethylene hydrogenated castor oil, polyoxyethylene fatty amides and their monoethanolamine and diethanolamine derivatives, and polyethoxylated fatty amines, with a number of ethylene oxide groups of at least about 50, and mixtures thereof.

Among preferred nonionic surfactants comprising one or more polyethyleneoxide chain include polyoxyethylene alkyl ethers having at least about 5, preferably from about 10 to 20, ethylene oxide units. Examples of such nonionic surfactants are steareth-10 and steareth-15.

Any such surfactant known in the art for use in hair or personal care products may be used, provided that the additional surfactant is also chemically and physically compatible with the essential components of the composition, or does not otherwise unduly impair product performance, aesthetics or stability. The concentration of the additional surfactants in the composition may vary with the cleansing or lather performance desired, the optional surfactant selected, the desired product concentration, the presence of other components in the composition, and other factors well known in the art.

Non-limiting examples of other anionic, zwitterionic, amphoteric, cationic, nonionic, or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; and 2,528,378.

Dispersed Gel Network Phase

The shampoo compositions also comprise a dispersed gel network phase comprising at least one fatty acid. The gel network phase is included in the shampoo compositions to provide conditioning benefits. As used herein, the term "gel network" refers to a lamellar or vesicular solid crystalline phase which comprises at least one fatty acid as specified below, and at least one secondary component selected from at least one secondary surfactant or an additional fatty amphiphile, as specified below, and water or other suitable solvents. The lamellar or vesicular phase comprises bi-layers made up of a first layer comprising the fatty acid and the secondary surfactant and/or fatty amphiphile, and alternating with a second layer comprising the water or other suitable solvent. The term "solid crystalline", as used herein, refers to the structure of the lamellar or vesicular phase which forms at a temperature below the chain melt temperature of the layer in the gel network comprising the one or more fatty acids, the chain melt temperature of the gel network phase being at least about 27° C. Preferably, the chain melt temperature should be at least 30° C., and even more preferably, it should be greater than or equal to 34° C. The chain melt temperature may be measured by differential scanning calorimetry, a method of which is described in the Examples below.

Gel networks which comprise, for example, fatty alcohols have been used for years in cosmetic creams and hair conditioners. Such cosmetic creams and hair conditioners, however, typically contain very low amounts, if any, of detersive surfactant. Thus, such known products do not provide a combination of cleansing and conditioning to the hair or skin.

Gel networks, generally, are further described by G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M. Eccleston, "The Microstructure of Semisolid Creams", *Pharmacy International, Vol.* 7, 63-70 (1986).

In one embodiment, the dispersed gel network phase is pre-formed. The term "pre-formed", as used herein, means that the mixture of the fatty acid, with the secondary surfactant and/or additional fatty amphiphile, and water or other suitable solvent is substantially a solid crystalline phase when added to the other components of the shampoo composition.

The cooled and pre-formed gel network component subsequently is added to the other components of the shampoo composition, including the detersive surfactant component. While not intending to be limited by theory, it is believed that incorporation of the cooled and pre-formed gel network component with the detersive surfactant and other components of the shampoo composition allows the formation of a substantially equilibrated lamellar dispersion ("ELD") in the final shampoo composition. The ELD is a dispersed lamellar or vesicular phase resulting from the pre-formed gel network component substantially equilibrating with the detersive surfactants, water, and other optional components, such as salts, which may be present in the shampoo composition. This equilibration occurs upon incorporation of the pre-formed gel network component with the other components of the shampoo composition and is effectively complete within about 24 hours after making. Shampoo compositions in which the ELD is formed provide hair with improved wet and dry conditioning benefits. Further, the ELD does not form if the components which comprise the gel network component (i.e., the fatty acid, secondary surfactant, and/or additional fatty amphiphile combined with water) are added as individual components together with the other components of the shampoo composition in one mixing step, and not as a separate cooled pre-formed gel network component.

The presence of the gel network in the pre-mix and in the final shampoo composition in the form of the ELD can be confirmed by means known to one of skill in the art, such as X-ray analysis, optical microscopy, electron microscopy, and differential scanning calorimetry. Methods of X-ray analysis and differential scanning calorimetry are described in the Examples below.

The aforementioned dispersed gel network phase is described as a phase which may be formed by combining one or more fatty acids with one or more secondary surfactants and/or an additional fatty amphiphile with water or a suitable solvent. Suitable solvents other than water include glycerin or other hydrophilic solvents. Therefore, in one embodiment, the dispersed gel network phase may be formed by combining one or more fatty acids with one or more secondary surfactants and water, or a suitable solvent. In another embodiment, the dispersed gel network phase may be formed by combining one or more fatty acids with one or more additional fatty amphiphiles and water, or a suitable solvent. The term "additional fatty amphiphile" as used herein, means any amphiphile other than a fatty acid.

In one embodiment, the weight ratio of the fatty acid to the secondary surfactant in the dispersed gel network component is greater than about 1:9, preferably from greater than about 1:5 to about 100:1, more preferably from greater than about 1:1 to about 40:1, and even more preferably greater than about 2:1 to about 10:1.

In another embodiment, the weight ratio of the fatty acid to the additional fatty amphiphile is from about 10:1 to about 1:5, more preferably from about 8:1 to about 1:4, and most preferably from about 6:1 to about 1:4.

The aforementioned ratios are important for proper and increasingly optimal formation of the gel network phase.

In yet another embodiment, the fatty acid may be combined with both a secondary surfactant and an additional fatty amphiphile to form the aforementioned gel network. In such cases, the aforementioned ratios of fatty acid to the additional fatty amphiphile and of the fatty acid to the secondary surfactant generally apply to gel networks formed by the presence of each of the fatty acid, additional fatty amphiphile and secondary surfactant.

The shampoo composition of the present invention comprise a gel network in an amount greater than about 0.1%, preferably from about 1% to about 60%, and more preferably from about 5% to about 40%, by weight of the shampoo composition.

Fatty Acid/Alkoxylated Fatty Acid

As discussed above, the primary ingredient used to form the gel network phase is a fatty acid. Suitable fatty acids may be generally defined as fatty acids or alkoxylated fatty acid compounds. More specifically, the fatty acids or alkoxylated fatty acid compounds should generally conform to the following formula:

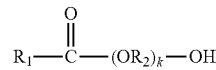

wherein $R_1$ is as described above; $R_2$ is a $C_1$-$C_5$ carbon chain which can be branched or hydroxy substituted; and k is a number ranging from about 0 to about 5.

Non-limiting examples of suitable fatty acids and alkoxylated fatty acids include behenic acid, stearic acid, C10-40 hydroxyalkyl acid, C32-36 isoalkyl acid coconut acid, erucic acid, hydroxystearic acid, lauric acid, linoleic acid, myristic acid, oleic acid, palmitic acid, PEG-8 behenate, PEG-5 cocoate, PEG-10 cocoate, PEG-2 laurate, PEG-4 laurate PEG-6 laurate, PEG-8 laurate, PEG-9 laurate, PEG-10 laurate, PEG-7 oleate, PEG-2 stearate, PEG-3 stearate, PEG-4 stearate, PEG-5 stearate, PEG-6 stearate, PEG-7 stearate, PEG-8 stearate, PEG-9 stearate, PEG-10 stearate, polyglyceryl-2-PEG-4 stearate, PPG-2 isostearate, and PPG-9 laurate.

Additional Fatty Amphiphile

The gel network component of the present invention may comprise at least one additional fatty amphiphile. As used herein, "fatty amphiphile" refers to a compound having a hydrophobic tail group of $R_1$ as defined below and a hydrophilic head group which does not make the compound water soluble, wherein the compound also has a net neutral charge at the pH of the shampoo composition. The term "water soluble", as used herein, means that the material is soluble in water in the present composition. In general, the material should be soluble at 25° C. at a concentration of 0.1% by weight of the water solvent, preferably at 1%, more preferably at 5%, more preferably at 15%.

The fatty amphiphile may be characterized as a compound having a Hydrophilic-Lipophilic Balance ("HLB") of 6 or less. The HLB, as used herein, is the standard HLB according to Griffin, J. Soc. Cosm. Chem., vol. 5, 249 (1954).

The shampoo compositions may comprise an additional fatty amphiphile as part of the pre-formed dispersed gel network phase in an amount from about 0.05% to about 14%, preferably from about 0.5% to about 10%, and more preferably from about 1% to about 8%, by weight of the shampoo composition.

Suitable fatty amphiphiles, or suitable mixtures of two or more fatty amphiphiles, have a melting point of at least about 27° C. The melting point, as used herein, may be measured by a standard melting point method as described in U.S. Pharmacopeia, USP-NF General Chapter <741> "Melting range or temperature". The melting point of a mixture of two or more materials is determined by mixing the two or more materials at a temperature above the respective melt points and then allowing the mixture to cool. If the resulting composite is a homogeneous solid below about 27° C., then the mixture has a suitable melting point for use in the present invention. A mixture of two or more fatty amphiphiles, wherein the mixture comprises at least one fatty amphiphile having an individual melting point of less than about 27° C., still is suitable for use in the present invention provided that the composite melting point of the mixture is at least about 27° C.

Suitable fatty amphiphiles have a hydrophobic tail group of $R_1$. As used herein, $R_1$ is an alkyl, alkenyl (containing up to 3 double bonds), alkyl aromatic, or branched alkyl group of $C_{12}$-$C_{70}$ length. Non-limiting examples of alkyl, alkenyl, or branched alkyl groups suitable for the fatty amphiphiles of the present invention include lauryl, tridecyl, myristyl, pentadecyl, cetyl, heptadecyl, stearyl, arachidyl, behenyl, undecylenyl, palmitoleyl, oleyl, palmoleyl, linoleyl, linolenyl, arahchidonyl, elaidyl, elaeostearyl, erucyl, isolauryl, isotridecyl, isomyristal, isopentadecyl, petroselinyl, isocetyl, isoheptadecyl, isostearyl, isoarachidyl, isobehnyl, gadoleyl, brassidyl, and technical-grade mixture thereof.

As used herein, $R_1$ also may be a branched alkyl group prepared by alkaline condensation of alcohols to give higher molecular weight, branched isoalcohols. These branched isoalcohols are referred to in the art as Guerbet alcohols.

$R_1$ may be alkyl, alkenyl or branched carbon chains of vegetable origin, such as wheat germ, sunflower, grape seed, sesame, maize, apricot, castor, avocado, olive, soybean, sweet almond, palm, rapeseed, cotton seed, hazelnut, macadamia, karite, jojoba, alfalfa, poppy, pumpkinseed, sesame, cucumber, blackcurrant, evening primrose, millet, barley, quinoa, rye, safflower, candlenut, passion flower or musk rose oil, and karite butter.

Suitable additional fatty amphiphiles also have a hydrophilic head group which does not make the compound water soluble, such as in compounds having an HLB of 6 or less.

Non-limiting examples of classes of compounds having such a hydrophilic head group include fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, fatty diesters, fatty sorbitan esters, fatty sugar esters, methyl glucoside esters, fatty glycol esters, mono, di & tri glycerides, polyglycerine fatty esters, alkyl glyceryl ethers, propylene glycol fatty acid esters, cholesterol, ceramides, fatty silicone waxes, fatty glucose amides, and phospholipids.

As discussed above, the "additional fatty amphiphile" of the present invention is a fatty amphiphile which is selected from among fatty amphiphiles which are not fatty acids or alkoxylated fatty acids. Accordingly, the "additional fatty amphiphile" used to form a gel network phase is not a fatty acid or alkoxylated fatty acid.

To form the gel network component of the present invention, individual fatty amphiphile compounds or combinations of two or more different fatty amphiphile compounds may be selected.

Secondary Surfactant

The gel network component of the present invention also comprises a secondary surfactant. As used herein, "secondary surfactant" refers to one or more surfactants which are combined with the fatty amphiphile and water to form the gel network of the present invention as a pre-mix separate from the other components of the shampoo composition. The secondary surfactant is separate from and in addition to the detersive surfactant component of the shampoo composition. However, the secondary surfactant may be the same or different type of surfactant or surfactants as that or those selected for the detersive surfactant component described above.

Although various suitable secondary surfactants are listed below, nonionic and anionic secondary surfactants are not particularly desirable for the formation of fatty acid gel networks. Therefore, where secondary surfactants are present in the formation of the gel network phase, cationic surfactants are preferred. In the instance when the gel network phase is formed in the absence of an additional fatty amphiphile, cationic surfactants are even more preferred. The other types of secondary surfactants listed below are otherwise suitable to gel networks comprising other types of fatty amphiphiles of the present invention.

The secondary surfactant component may be present as part of the pre-formed dispersed gel network phase in an amount from about 0.01% to about 15%, preferably from about 0.1% to about 10%, and more preferably from about 0.3% to about 5%, by weight of the shampoo composition.

Cationic surfactants suitable for use as secondary surfactants of the present invention include quaternary ammonium salts or amido-amines having at least one fatty chain containing at least about 8 carbon atoms and mixture thereof.

Suitable quaternary ammonium salts have the following general formula:

wherein $R_1$ is selected from linear and branched radicals comprising from about 8 to about 12 carbon atoms; $R_2$ is selected from linear and branched radicals comprising from about 8 to 12 carbon atoms or the same group as radicals $R_3$ and $R_4$; $R_3$ and $R_4$ are independently selected from linear and branched aliphatic radicals comprising from about 1 to about 4 carbon atoms, and aromatic radicals such as aryl and alkylaryl, wherein the aliphatic radicals may comprise at least one hetero atom such as oxygen, nitrogen, sulphur, and halogens, and the aliphatic radicals are chosen, for example, from alkyl, alkoxy, and alkylamide radicals; and X— is an anion selected from halides such as chloride, bromide, and iodide, ($C_2$-$C_6$) alkyl sulphates, such as methyl sulphate, phosphates, alkyl, and alkylaryl sulphonates, and anions derived from organic acids, such as acetate and lactate.

Non-limiting examples of such suitable cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, and mixtures thereof.

Suitable amido-amine cationic surfactants have the following general formula:

$$R'_1\text{—CONH}(CH_2)nNR'_2R'_3$$

wherein $R'_1$ is selected from linear and branched radicals comprising about 8 to about 12 carbon atoms; $R'_2$ and $R'_3$ are independently selected from hydrogen, linear and branched aliphatic radicals comprising from about 1 to about 4 carbon atoms, and aromatic radicals such as aryl and alkylaryl, wherein the aliphatic radicals may comprise at least one hetero atom such as oxygen, nitrogen, sulphur, and halogens, and the aliphatic radicals are chosen, for example, from alkyl, alkoxy and alkylamide radicals; and n is an integer from about 1 to about 4.

Non-limiting examples of such suitable amido-amines include stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

Various other secondary surfactants include anionic, zwitterionic, amphoteric, cationic, and nonionic surfactants as generally described above.

Preferred anionic surfactants for use as secondary surfactants of the present invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, sodium cocoyl isethionate, and combinations thereof.

Suitable nonionic surfactants include nonionic surfactants having an HLB of 7 or more and comprising one or more polyethyleneoxide chains wherein each polyethyleneoxide chain contains on average at least about 5 ethylene oxide units.

Nonionic surfactants comprising one or more polyethyleneoxide chain wherein each polyethyleneoxide chain contains on average at least about 5 ethylene oxide units include polyoxyethylene alkyl ethers, polyethyleneglycol fatty acid esters, polyoxyethylene castor oil, polyoxyethylene hydrogenated castor oil, polyoxyethylene fatty amides and their monoethanolamine and diethanolamine derivatives, and polyethoxylated fatty amines, with a number of ethylene oxide groups of at least about 5, and mixtures thereof.

Among preferred nonionic surfactants comprising one or more polyethyleneoxide chain include polyoxyethylene alkyl ethers having at least about 5, preferably from about 10 to 20, ethylene oxide units. Examples of such nonionic surfactants are steareth-10 and steareth-15.

Also suitable for use as nonionic surfactants are nonionic surfactants having an HLB of 7 or more which are free of polyethyleneoxide chains. Nonionic surfactants free of polyethyleneoxide chains include polyglycerolated fatty acids, polyglycerolated fatty amides, polyglycerolated alkyl phenols, polyglycerolated α-diols, polyglycerolated alcohols, alkyl polyglucosides, and sugar esters. Preferably, suitable nonionic surfactants free of polyethyleneoxide chains are selected from alkyl polyglucosides, sugar esters, polyglyceryl fatty acid esters, alkyl polyglyceryl ethers, and mixtures thereof.

Other suitable secondary surfactants also include so-called gemini surfactants. Gemini surfactants are generally described by F. M. Menger and C. A. Littau, "Gemini Surfactants: A New Class of Self-Assembling Molecules", *J. Am. Chem. Soc.* 1993, 115, 10083-10090; and by B. S. Sekon, "Gemini (dimeric) Surfactants: The Two Faced Molecules", *Resonance*, 42-49 (March 2004). Examples of suitable gemini surfactants are described in U.S. Pat. Nos. 5,922,671; 6,204,297; 6,358,914; 6,710,022; 6,777,384; 6,794,345; and 6,797,687.

More than one surfactant of the above specified types may be used for the secondary surfactant of the present invention.

Water

The gel network component also comprises water or suitable solvents. The water and the secondary surfactant and/or additional fatty amphiphile, together, aid the swelling of the fatty acid. This, in turn, leads to the formation and the stability of the gel network. The shampoo compositions comprise water as part of the pre-formed dispersed gel network phase in an amount suitable to achieve a gel network when combined with fatty acid, additional fatty amphiphile, and/or the secondary surfactant.

In a preferred embodiment, the shampoo compositions comprise as part of the pre-formed dispersed gel network phase at least about 0.05% of water, by weight of the shampoo composition.

In another embodiment of the present invention, the shampoo compositions comprise water as part of the pre-formed dispersed gel network phase is an amount relative to the amount of fatty acid at a weight ratio of at least about 1:1.

Aqueous Carrier

The shampoo compositions of the present invention comprise an aqueous carrier. Typically, the compositions of the present invention are in the form of pourable liquids (under ambient conditions). The compositions, therefore, comprise an aqueous carrier at a level of from about 20% to about 95%, preferably from about 60% to about 85%, by weight of the compositions. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

Additional Components

The compositions of the present invention may further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10% by weight of the compositions.

Non-limiting examples of optional components for use in the composition include cationic polymers, conditioning agents (hydrocarbon oils, fatty esters, silicones), anti-dandruff agents, suspending agents, viscosity modifiers, dyes, nonvolatile solvents or diluents (water soluble and insoluble), pearlescent aids, foam boosters, additional surfactants or nonionic cosurfactants, pH adjusting agents, perfumes, preservatives, chelants, proteins, skin active agents, sunscreens, UV absorbers, and vitamins.

Deposition Aid

The shampoo compositions may include a deposition aid. The deposition aid is included to effectively enhance deposition of the gel network component. The deposition aid can comprise any material that enhances the deposition of the gel network from the shampoo onto the hair and/or scalp.

The concentration of the deposition aid in the shampoo composition should be sufficient to effectively enhance the deposition of the gel network component and ranges from about 0.05% to about 5%, preferably from about 0.075% to about 2.5%, more preferably from about 0.1% to about 1.0%, by weight of the shampoo composition.

In one embodiment of the present invention, the deposition aid is a cationic polymer. Preferred cationic polymers will have cationic charge densities of at least about 0.6 meq/g, preferably at least about 1.2 meq/g, more preferably at least about 1.5 meq/g, but also preferably less than about 7 meq/g, more preferably less than about 5 meq/g, at the pH of intended use of the composition. The pH will generally range from about pH 3 to about pH 9, preferably between about pH 4 and about pH 8. The "cationic charge density" of a polymer, as that term is used herein, refers to the ratio of the number of positive charges on the polymer to the molecular weight of the polymer. The average molecular weight of such suitable cationic polymers will generally be between about 10,000 and 10 million, preferably between about 50,000 and about 5 million, more preferably between about 100,000 and about 3 million.

Suitable cationic polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate.

Non-limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Non-limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). Preferred cationic substituted monomers are the cationic substituted dialkylaminoalkyl acrylamides, dialkylaminoalkyl methacrylamides, and combinations thereof. These preferred monomers conform the to the formula

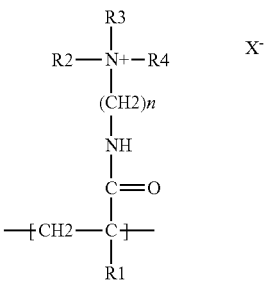

wherein $R^1$ is hydrogen, methyl or ethyl; each of $R^2$, $R^3$ and $R^4$ are independently hydrogen or a short chain alkyl having from about 1 to about 8 carbon atoms, preferably from about 1 to about 5 carbon atoms, more preferably from about 1 to about 2 carbon atoms; n is an integer having a value of from about 1 to about 8, preferably from about 1 to about 4; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups a non limiting example of which is polymethyacrylamidopropyl trimonium chloride, available under the trade name Polycare 133, from Rhone-Poulenc, Cranberry, N.J., U.S.A. Also preferred are copolymers of the above cationic monomer with nonionic monomers such that the charge density of the total copolymer is from about 2.0 meq/g to about 4.5 meq/g.

Other suitable cationic polymers for use in the composition include polysaccharide polymers, such as cationic cellulose derivatives and cationic starch derivatives. Suitable cationic polysaccharide polymers include those which conform to the formula

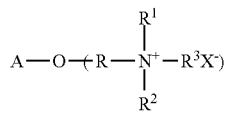

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

Other Optional Components

Non-limiting examples of other optional components include dispersed particles, nonionic polymers, conditioning agents such as non-volatile silicone oils, cationic silicones, silicone gums, high refractive silicones, silicone resins, organic conditioning oils, hydrocarbon oils, polyolefins, fatty esters, and combinations thereof.

Other optional components which are contemplated include antidandruff agents, humectants, suspending agents such as hydrogenated castor oils, xanthan gum, and crosslinked acrylic acid polymers, Process of Making a Shampoo Composition An aspect of the invention relates to a process of making a shampoo composition comprising a dispersed solid crystalline gel network phase. The process of making the shampoo composition comprises (a) combining one or more fatty acids, a secondary surfactant and/or an additional fatty amphiphile, and water at a temperature (above the chain melt temperature of the premix) sufficient to allow partitioning of the secondary surfactant and the water into the fatty acid(s) to form a pre-mix; (b) cooling the pre-mix below the chain melt temperature of the fatty acid(s) to form a gel network; (c) adding the gel network to one or more detersive surfactants and an aqueous carrier to form a shampoo composition.

As discussed above, in one embodiment, the gel network component is prepared as a separate pre-mix, which, after being cooled, is subsequently incorporated with the other components of the shampoo composition. More specifically, the gel network component of the present invention may be prepared by heating the fatty acid(s), the secondary surfactant and/or additional fatty amphiphile, and water to a level in the range of about 75° C. to about 90° C. and mixing. This mixture is cooled to a level in the range of about 27° C. to about 35° C. by, for example, passing the mixture through a heat exchanger. As a result of this cooling step, the fatty acid(s), secondary surfactant(s), and/or additional fatty amphiphile crystallize to form a crystalline gel network.

Alternative methods of preparing the gel network component include sonication and/or milling of the fatty acid(s), the secondary surfactant and/or additional fatty amphiphile, and water, while these components are heated, to reduce the particle size of the melted fatty acid phase. This results in an increase in surface area of the fatty acid phase, which allows the secondary surfactant and/or additional fatty acid and the water to swell the fatty acid phase. Another suitable variation in preparing the gel network includes heating and mixing the fatty acid(s), the secondary surfactant, and/or the additional fatty amphiphile first, and then adding that mixture to the water.

NON-LIMITING EXAMPLES

The shampoo compositions illustrated in the following Examples illustrate specific embodiments of the shampoo compositions of the present invention, but are not intended to be limiting thereof. Other modifications can be undertaken by the skilled artisan without departing from the spirit and scope of this invention. These exemplified embodiments of the shampoo composition of the present invention provide enhanced conditioning benefits to the hair.

The shampoo compositions illustrated in the following Examples are prepared by conventional formulation and mixing methods, an example of which is set forth hereinbelow. All exemplified amounts are listed as weight percents and exclude minor materials such as diluents, preservatives, color solutions, imagery ingredients, botanicals, and so forth, unless otherwise specified. All percentages are based on weight unless otherwise specified.

Preparation of the Gel Network Pre-Mix

To prepare the gel network pre-mix, about 20% of the water is heated to about 80° C. and the fatty acid, other additional fatty amphiphiles and/or the secondary surfactant (e.g., Behenyltrimethylammonium chloride (Varisoft BT-85)) are added to it. After incorporation, this mixture pH is adjusted with NaOH as needed to achieve the target pH of 4-8 and is passed through a mill and heat exchanger where it is cooled to about 35° C. As a result of this cooling step, the fatty acid, the secondary surfactant and/or additional fatty amphiphile, and the water form a crystalline gel network.

To prepare the gel network pre-mix utilizing at least one fatty acid and at least one additional fatty amphiphile in the absence of the secondary surfactant, about 20% of the water is heated to about 80° C. and the fatty acid and additional fatty amphiphile are added to it. After incorporation, this mixture pH is adjusted with NaOH as needed to achieve the target pH of 6-8 and is passed through a mill and heat exchanger where it is cooled to about 35° C. As a result of this cooling step, the fatty acid, additional fatty amphiphile and the water form a crystalline gel network.

For mixtures of different fatty acids with other fatty amphihiles, it may be beneficial to pre-mix the fatty acid and other fatty amphiphile materials before incorporation into the water. This can be done by co-melting the different fatty acids and fatty amphiphiles together and utilizing this melt or cooling into a solid phase and incorporating this into the heated water along with the secondary surfactant. Another variation could be to co-melt the one or more fatty acids and fatty amphiphiles and the secondary surfactant before incorporation into the water. Some gel network compositions with chain melt temperatures between about 27° C. to about 35° C. will need to be cooled below 27° C. to ensure the lamellar phase structure is froze.

Gel Network Pre-Mix Examples

The following Examples illustrate specific embodiments of the gel network pre-mix, prior to its incorporation with the detersive surfactant and other components of the final shampoo composition of the present invention. It is intended that each of the following gel network pre-mix examples could be incorporated as a dispersed phase into a shampoo composition according to the present invention.

| Ingredient | 1 | 2 | 3 | 4 | 5 | 6 | 7 |
|---|---|---|---|---|---|---|---|
| Water | 88.22% | 88.22% | 86.46% | 87.75% | 88.55% | 80.68% | 78.66% |
| Palmitic Acid V-1695 (3) | 2.24% | | | 6.36% | 5.72% | 7.41% | |
| Cetyl Alcohol | | | | | | 3.86% | 4.06% |
| Lauric Acid | | 2.24% | | | | | |
| Steary Alcohol | | | | | | 7.73% | 7.97% |
| Behenic Acid (2) | | | 3.47% | | | | |
| Stearic acid, V-1890 (3) | 4.47% | 4.47% | 6.93% | 3.01% | 2.86% | | 8.23% |
| Behenyltrimethylammonium chloride, Varisoft BT-85 85% Active in isopropanol (4) | 5.04% | 5.04% | 3.11% | 2.85% | 2.84% | | |
| 50% NaOH Solution | | | | | | 0.29% | 0.52% |
| 5-Chloro-2-methyl-4-isothiazolin-3-one, Kathon CG | 0.03% | 0.03% | 0.03% | 0.03% | 0.03% | 0.03% | 0.03% |
| Good Lameller Structure Observed with SAXS? | Yes | Yes | Yes | Yes | Yes | Yes | Yes |

| Ingredient | 8 | 9 | 10 | 11 | 12 | 13 | 14 |
|---|---|---|---|---|---|---|---|
| Water | 87.74% | 88.97% | 88.97% | 88.22% | 89.97% | 88.82% | 88.62% |
| Palmitic Acid, V-1695 (3) | 4.47% | 2.24% | 2.24% | 4.47% | 2.00% | | 2.42% |
| Cetyl Alcohol | | | | | | 2.24% | 2.86% |
| Steareth-20 | | | | | 4.00% | | |
| Stearyl Alcohol | | | | | | 4.47% | 5.72% |
| Sodium Cetyl/Stearyl Sulfate (1) | | | 4.29% | | | | |
| Stearic acid, V-1890 (3) | 2.24% | 4.47% | 4.47% | 2.24% | 4.00% | 4.29% | |
| Behenyltrimethylammonium chloride, Varisoft BT-85, 85% Active in isopropanol (4) | 5.04% | | | 5.04% | | | |
| Behenyl Sulfate (3) | | 4.29% | | | | | |
| 50% NaOH Solution | 0.48% | | | | | 0.15% | 0.35% |
| 5-Chloro-2-methyl-4-isothiazolin-3-one, Kathon CG | 0.03% | 0.03% | 0.03% | 0.03% | 0.03% | 0.03% | 0.03% |
| Good Lameller Structure Observed with SAXS? | Yes, see below | No, see below | No | Yes | No, see below | Yes | Yes |

(1) available from Cognis Chemicals as Lanette E
(2) available from Croda Chemicals
(3) available from P&G Chemicals
(4) available Goldschmidt Chemical Preparation of Final Shampoo Compositions To prepare the final shampoo composition, first, a surfactant solution pre-mix is formed. To prepare this surfactant solution pre-mix, about 6% to about 9% of sodium or ammonium laureth-3 sulfate, cationic polymers, and about 0% to about 5% of water are added to a jacketed mix tank and heated to about 74° C. with agitation. To this solution, citric acid, sodium citrate, sodium benzoate, and disodium EDTA are added to the tank and allowed to disperse. Ethylene glycol distearate (EGDS) is then added to the mixing vessel and melted. After the EGDS was well dispersed (e.g., after about 10 minutes), preservative is added and mixed into the surfactant solution. This mixture is passed through a mill and heat exchanger where it is cooled to about 35° C. and collected in a finishing tank. As a result of this cooling step, the EGDS crystallizes to form a waxy crystalline suspension. The mixture of these components is the surfactant solution pre-mix.

Next, the surfactant solution pre-mix and the gel network pre-mix, which is prepared as described above, are mixed together. The remainder of the surfactants, perfume, dimethicone, sodium chloride or ammonium xylene sulfonate for viscosity adjustment, and the remainder of the water are added with ample agitation to ensure a homogeneous mixture. This mixture is the final shampoo composition which comprises as a dispersed phase the gel network pre-mix.

Preferred viscosities of the final shampoo composition according to the present invention range from about 5000 to about 15,000 centipoise at 27° C., as measured by a Wells-Brookfield model RVTDCP viscometer using a CP-41 cone and plate at 2/s at 3 minutes.

The pH may be adjusted as necessary to provide shampoo compositions of the present invention which are suitable for application to human hair, and may vary based on the selection of particular detersive surfactants, fatty acids, and/or other components.

Shampoo Examples

The following Examples illustrate specific embodiments of the final shampoo composition of the present invention, which respectively comprise select above-exemplified gel network pre-mixes as a dispersed phase.

| Ingredient | 1 | 2 | 3 | 4 | 5 | 6 | 7 | 8 | 9 | 10 |
|---|---|---|---|---|---|---|---|---|---|---|
| Sodium Laureth Sulfate | 10.00 | 10.00 | 10.00 | 10.00 | 10.00 | 4.89 | 5.22 | 6.57 | 7.92 | 9.85 |
| Sodium Lauryl Sulfate | 1.50 | 1.50 | 1.50 | 1.50 | 1.50 | 3.58 | 4.13 | 1.99 | 2.42 | 2.98 |
| Cocamidopropyl betaine | 2.00 | 2.00 | 2.00 | 2.00 | 2.00 | 3.72 | 4.02 | 4.02 | 3.26 | 4.02 |
| Cocamide MEA | | | | | | | | | 2.37 | |
| Gel Network 4 | | | | | | | | 20.56 | 24.77 | 30.84 |
| Gel Network 7 | | | | | | 19.03 | 21.95 | | | |
| Gel Network 8 | 27.3 | | | | | | | | | |
| Gel Network 9 | | 27.3 | | | | | | | | |
| Gel Network 7 | | | | | | | | | | |
| Gel Network 11 | | | 27.3 | | | | | | | |
| Gel Network 12 | | | | 27.3 | | | | | | |
| Gel Network 13 | | | | | 27.3 | | | | | |
| Guar Hydroxypropyl trimonium chloride (3) | 0.40 | 0.40 | 0.40 | 0.40 | 0.40 | 0.20 | 0.21 | 0.54 | | 0.40 |
| Polyquaterium-10 (4) | | | | | | | | | 0.32 | |
| Dimethicone (6) | 2.00 | 2.00 | 2.00 | 2.00 | 2.00 | 2.79 | 2.14 | | | |
| Ethylene Glycol Distearate | 1.50 | 1.50 | 1.50 | 1.50 | 1.50 | 1.50 | 1.50 | 1.50 | 1.50 | 1.50 |
| 5-Chloro-2-methyl-4-isothiazolin-3-one, Kathon CG | 0.0005 | 0.0005 | 0.0005 | 0.0005 | 0.0005 | 0.0006 | 0.0006 | 0.0006 | 0.0006 | 0.0006 |
| Sodium Benzoate | 0.25 | 0.25 | 0.25 | 0.25 | 0.25 | 0.25 | 0.25 | 0.25 | 0.25 | 0.25 |
| Disodium EDTA | 0.13 | 0.13 | 0.13 | 0.13 | 0.13 | 0.14 | 0.14 | 0.14 | 0.14 | 0.14 |
| Perfume | 0.70 | 0.70 | 0.70 | 0.70 | 0.70 | 0.65 | 0.65 | 0.65 | 0.65 | 0.65 |
| Citric Acid/Sodium Citrate Dihydrate | pH QS | pH QS | pH QS | pH QS | pH QS | pH QS | pH QS | pH QS | pH QS | pH QS |
| Sodium Chloride/Ammonium Xylene Sulfonate | Visc. QS | Visc. QS | Visc. QS | Visc. QS | Visc. QS | Visc. QS | Visc. QS | Visc. QS | Visc. QS | Visc. QS |
| Water | QS | QS | QS | QS | QS | QS | QS | QS | QS | QS |

| Ingredient | 11 | 12 | 13 | 14 | 15 | 16 | 17 | 18 | 19 | 20 |
|---|---|---|---|---|---|---|---|---|---|---|
| Sodium Laureth Sulfate | | | 4.89 | 10.00 | 7.65 | 7.65 | 7.65 | | | 7.65 |
| Sodium Lauryl Sulfate | | | 8.97 | 1.50 | 6.35 | 6.35 | 6.35 | | | 6.35 |
| Ammonium Laureth Sulfate | 10.00 | 6.00 | | | | | | 12.00 | 10.00 | |
| Ammonium Lauryl Sulfate | 6.00 | 10.00 | | | | | | 2.00 | 2.00 | |
| Sodium Lauroamphoacetate | | | | | | | | 2.00 | 2.00 | |
| Cocamidopropyl betaine | | | | 2.00 | | | | | 2.00 | |
| Cocamide MEA | | | 1.93 | | | | | 0.60 | | |
| Any one of Gel Networks 1-14 | 27.27 | 27.27 | | 27.27 | 27.27 | 13.64 | 6.82 | 27.27 | 27.27 | 27.27 |

-continued

| | | | | | | | | | | |
|---|---|---|---|---|---|---|---|---|---|---|
| Gel Network 3 | | 15.29 | | | | | | | | |
| Guar Hydroxypropyl trimonium chloride (1) | 0.15 | | | | | | | | | |
| Guar Hydroxypropyl trimonium chloride (2) | | | 0.5 | | | | 0.60 | | | |
| Guar Hydroxypropyl trimonium chloride (3) | | | | 0.40 | 0.40 | 0.40 | | | | |
| Polyquaterium-10 (4) | | 0.20 | | | | | | | | 0.10 |
| Polyquaterium-10 (5) | 0.4 | | | | | | | | | |
| Dimethicone (6) | 2.00 | 2.00 | 0.85 | 2.00 | 2.00 | 2.00 | 2.00 | | | 2.00 |
| Dimethicone (7) | | | | | | | | 2.00 | 2.00 | |
| Zinc Pyrithione | 1.00 | | | | | | | | | |
| Ethylene Glycol Distearate | 1.50 | 1.50 | 1.50 | 1.50 | 1.50 | 1.50 | 1.50 | 1.50 | 1.50 | 1.50 |
| 5-Chloro-2-methyl-4-isothiazolin-3-one, Kathon CG | 0.0005 | 0.0005 | 0.0006 | 0.0005 | 0.0005 | 0.0005 | 0.0005 | 0.0005 | 0.0005 | 0.0005 |
| Sodium Benzoate | 0.25 | 0.25 | 0.25 | 0.25 | 0.25 | 0.25 | 0.25 | 0.25 | 0.25 | 0.25 |
| Disodium EDTA | | 0.14 | 0.13 | 0.13 | 0.13 | 0.13 | 0.13 | 0.13 | 0.13 | 0.13 |
| Perfume | 0.70 | 0.65 | 0.70 | 0.70 | 0.70 | 0.70 | 0.70 | 0.70 | 0.70 | 0.70 |
| Citric Acid/Sodium Citrate Dihydrate | pH QS | pH QS | pH QS | pH QS | pH QS | pH QS | pH QS | pH QS | pH QS | pH QS |
| Sodium Chloride/Ammonium Xylene Sulfonate | Visc. QS | Visc. QS | Visc. QS | Visc. QS | Visc. QS | Visc. QS | Visc. QS | Visc. QS | Visc. QS | Visc. QS |
| Water | QS | QS | QS | QS | QS | QS | QS | QS | QS | QS |

(1) Jaguar C17 available from Rhodia
(2) N-Hance 3269 (with Mol. W. of ~500,000 and 0.8 meq/g) available from Aqulaon/Hercules
(3) ADPP-5043 HMW (with Mol. W. of ~1,200,000 and Char. Den. of 2.0 meq/g) available from Aqulaon/Hercules
(4) Polymer JR30M available from Amerchol/Dow Chemical
(5) Polymer LR30M available from Amerchol/Dow Chemical
(6) Viscasil 330M available from General Electric Silicones
(7) DC1664 available from Dow Corning Silicones The fatty acid deposition of these products is measured by treating a switch of hair with 3 cycles (2 lather/rinse steps per cycle, 0.1 g shampoo per g hair on each lather/rinse step) with the shampoo. Four switches are treated with each shampoo. The switches are then extracted with solvent and the level of adsorbed fatty acid is measured by gas chromatographic-mass spectrophotometric analysis of the extracts.

Analytical Methods and Examples

The following provides example X-ray analysis data and example differential scanning calorimetry ("DSC") data for several of the above-exemplified compositions.

| | X-Ray Data (SAXS) Lamellar d-spacing** | DSC Melt Transition Temperature for Gel Network* |
|---|---|---|
| Gel Network Example # 11 | 181 Å | 70° C. |
| Gel Network Example # 13 | 410 Å | 58° C. |
| Shampoo Example #3 with Gel Network Example #11 | 88 Å | 35° C. |
| Shampoo Example #5 with Gel Network Example #13 | 92 Å | 35° C. |

*See Differential Scanning Calorimetry method for sample preparation and analysis techniques.
**See X-Ray method for sample preparation and analysis techniques.

The Gel Network premix Example #8 has an XRD pattern that shows the presence of lamellar structure with a d-spacing of 104 Å that upon incorporation into the shampoo (Shampoo Example #1) shows the structure is preserved with a d-spacing of 88 Å. Whereas with Gel Network premix Examples #9 and #12, made with anionic and nonionic secondary surfactants respectively, there is either no or poorly defined lamellar structure seen and incorporation into the shampoo with shampoo examples #2 and #4 results in no defined lamellar structure observed.

Differential Scanning Calorimetry Method

The chain melt temperature of the layer in the gel network comprising the one or more fatty acids (i.e., the melt transition temperature for the gel network) may be obtained using differential scanning calorimetry according to the following method. Utilizing a TA Instruments Q100 DSC, approximately 50 mg of the gel network pre-mix or the final shampoo composition containing the gel network is placed into a stainless steel high volume DSC pan. The sample, along with an empty reference pan is placed into the instrument. The samples are analyzed using the following conditions/temperature program: Nitrogen Purge, Equilibrate @ 5.00° C. until an isothermal is reach for 2.00 min. Ramp the temperature at a rate of 3.00° C./min to 90.00° C. Each sample is analyzed in duplicate. The resulting DSC data is analyzed using TA Instruments Universal Analysis Software.

The use of DSC to measure the melt transition temperature for gel networks is further described by T. de Vringer et al., Colloid and Polymer Science, vol. 265, 448-457 (1987); and H. M. Ribeiro et al., Intl. J. of Cosmetic Science, vol. 26, 47-59 (2004).

X-Ray Analysis Method

Small-angle x-ray scattering ("SAXS") as used to resolve periodic structures in mesophases is essentially an x-ray diffraction technique. It is used in conjunction with conventional wide-angle x-ray diffraction ("WXRD") to characterize aggregate structures such as micelles, gel networks, lamella, hexagonal and cubic liquid crystals. The different mesophases that show periodic structures can be characterized by the relative positions (d-spacing) of their reflections as derived from the Bragg equation (d=$\lambda$/2 Sin $\theta$) where d represents the interplanar spacing, $\lambda$ the radiation wavelength and $\theta$ the scattering (diffraction) angle.

The one dimensional lamella gel network phase is characterized by the ratio of the interplanar spacings $d_1/d_1$, $d_1/d_2$, $d_1/d_3$, $d_1/d_4$, $d_1/d_5$ having the values 1:2:3:4:5 etc. in the SAXS region (long-range order) and one or two invariant reflection(s) in the WXRD region (short-range) centered around 3.5 and 4.5 Å over a broad halo background. Other mesophases (e.g. hexagonal or cubic) will have characteristically different d-spacing ratios.

WXRD data are collected in transmission mode on a Stoe STADI-P diffractometer equipped with an image plate position-sensitive detector. The specimen is positioned between two milar films in the sample holder and placed in the path of the x-ray beam. The IP detector has a solid angle of about 120° 2$\theta$ and records diffracted x-ray beams simultaneously. Data are collected and analyzed using the XPOW software.

SAXS data are collected on Rigaku rotating anode generator with a fine focus filament equipped with a HI-STAR 2-dimensional area detector from Bruker-AXS. The setup has an evacuated chamber, which houses the specimen, conjoined with an evacuated tube leading to the detector to reduce air scatter. The specimen sample holder consists of copper plates with small rectangular cavities to hold the fluid-like material and also allow the transmission of the x-ray beam. The openings to the cavities are sealed with kapton windows to provide leak-free environment under vacuum. The 2-D data are azimuthally integrated and reduced to intensity versus scattering vector (q) or its d equivalent by a combination of GADDS software and in-house software modules implementing known techniques on the Igor platform.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A shampoo composition comprising:
   a) from about 5% to about 50% of one or more anionic detersive surfactants, by weight of said shampoo composition;
   b) from about 5% to about 40% by weight of said shampoo composition of a pre-formed solid crystalline gel network phase consisting of:
      i) a fatty acid or alkoxylated fatty acid having a structure of

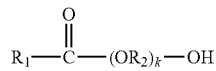

wherein R1 is C10-40 and $R_2$ is a $C_1$-$C_5$ carbon chain which can be branched or hydroxy substituted; and k is a number ranging from 0 to 5;
      ii) from about 0.05% to about 14% of one or more fatty amphiphiles by weight of said shampoo composition, wherein said fatty amphiphile is a fatty alcohol comprising a hydrophobic tail group selected from an alkyl group of $C_{12}$-$C_{70}$ length;
      iii) water; and
   wherein the weight ratio of said fatty acid or said alkoxylated fatty acid to said fatty alcohol is from about 10:1 to about 1:5 to form said pre-formed solid crystalline gel network phase; and
   c) from about 20% to about 95% of an aqueous carrier, by weight of said shampoo composition.

2. A shampoo composition according to claim 1, further comprising a deposition aid.

3. A shampoo composition according to claim 1, wherein said deposition aid is a cationic polymer.

4. A shampoo composition according to claim 3, wherein said cationic polymer has a molecular weight of from about 10,000 to about 10,000,000 and a charge density from about 0.6 meq/gm to about 7.0 meq/gm.

5. A shampoos composition according to claim 1 wherein the alkyl group is selected from the group consisting of: lauryl, tridecyl, myristyl, pentadecyl, cetyl, heptadecyl, stearyl, arachidyl, behenyl, undecylenyl, palmitoleyl, oleyl, palmoleyl, linoleyl, linolenyl, arahchidonyl, elaidyl, elaeostearyl, erucyl, isolauryl, isotridecyl, isomyristal, isopentadecyl, petroselinyl, isocetyl, isoheptadecyl, isostearyl, isoarachidyl, isobehnyl, gadoleyl, brassidyl, and mixtures thereof.

* * * * *